United States Patent
Cabrera-Munoz et al.

(10) Patent No.: US 11,045,167 B2
(45) Date of Patent: Jun. 29, 2021

(54) FORWARD-LOOKING ULTRASOUND ARRAY PROBE FOR INTRAVASCULAR IMAGING AND NAVIGATION APPLICATIONS

(71) Applicants: Nestor E. Cabrera-Munoz, Los Angeles, CA (US); Payam Eliahoo, Los Angeles, CA (US); Koping K. Shung, Monterey Park, CA (US)

(72) Inventors: Nestor E. Cabrera-Munoz, Los Angeles, CA (US); Payam Eliahoo, Los Angeles, CA (US); Koping K. Shung, Monterey Park, CA (US)

(73) Assignee: UNIVERSITY OF SOUTHERN CALIFORNIA, Los Angeles, CA (US)

( * ) Notice: Subject to any disclaimer, the term of this patent is extended or adjusted under 35 U.S.C. 154(b) by 986 days.

(21) Appl. No.: 15/325,547

(22) PCT Filed: Jul. 13, 2015

(86) PCT No.: PCT/US2015/040230
§ 371 (c)(1),
(2) Date: Jan. 11, 2017

(87) PCT Pub. No.: WO2016/010934
PCT Pub. Date: Jan. 21, 2016

(65) Prior Publication Data
US 2017/0156691 A1 Jun. 8, 2017

Related U.S. Application Data

(60) Provisional application No. 62/023,867, filed on Jul. 12, 2014.

(51) Int. Cl.
*A61B 8/12* (2006.01)
*A61B 8/00* (2006.01)
(Continued)

(52) U.S. Cl.
CPC ............ *A61B 8/12* (2013.01); *A61B 8/0891* (2013.01); *A61B 8/445* (2013.01); *A61B 8/4494* (2013.01); *A61B 8/461* (2013.01); *B06B 1/0607* (2013.01)

(58) Field of Classification Search
CPC ......... A61B 8/12; A61B 8/0891; A61B 8/445; A61B 8/4494; A61B 8/461; B06B 1/0607
(Continued)

(56) References Cited

U.S. PATENT DOCUMENTS

| | | | | |
|---|---|---|---|---|
| 5,920,972 A | * | 7/1999 | Palczewska | ............ B06B 1/064 29/25.35 |
| 2004/0100163 A1 | * | 5/2004 | Baumgartner | ........ B06B 1/0622 310/334 |

(Continued)

OTHER PUBLICATIONS

International Preliminary Report on Patentability for Application No. PCT/US2015/040230 dated Jan. 17, 2017 (6 pages).
(Continued)

*Primary Examiner* — Aaron F Roane
(74) *Attorney, Agent, or Firm* — Michael Best & Friedrich LLP

(57) ABSTRACT

An intraluminal forward-looking image producing device and associated methods of use and construction is disclosed. In particular, the device of the present invention is an intraluminal forward-looking intravascular ultrasound (IVUS) image producing device. The invention also encompasses methods of using the intraluminal forward-looking intravascular ultrasound (IVUS) image producing device to image objects and material in a forward direction. The disclosed methods also involve manufacturing the intraluminal forward-looking intravascular ultrasound (IVUS) image producing device including the piezoelectric transducer. The resulting device is an elongated body configured to fit within the lumen of a vessel and having an imaging
(Continued)

sensor located on the distal end of the elongated body configured to image objects and material in a forward direction. The method further involves inserting the intraluminal forward-looking intravascular ultrasound (IVUS) image producing device into a lumen of a vessel, and imaging objects or material in a forward direction. The methods of the present invention are particularly useful in vascular diagnostic and therapeutic procedures when the vessel has been completely blocked by plaque and imaging of the occlusion is required.

28 Claims, 11 Drawing Sheets

(51) Int. Cl.
  *B06B 1/06* (2006.01)
  *A61B 8/08* (2006.01)
(58) Field of Classification Search
  USPC .......................................................... 600/467
  See application file for complete search history.

(56) References Cited

U.S. PATENT DOCUMENTS

| | | | |
|---|---|---|---|
| 2004/0254471 A1* | 12/2004 | Hadjicostis | A61B 8/12 600/459 |
| 2009/0030312 A1* | 1/2009 | Hadjicostis | A61B 8/4488 600/439 |
| 2014/0180128 A1* | 6/2014 | Corl | B06B 1/0622 600/467 |
| 2015/0115773 A1* | 4/2015 | Li | A61B 8/12 310/335 |
| 2015/0164470 A1* | 6/2015 | Shiotani | A61B 8/4444 600/462 |

OTHER PUBLICATIONS

International Search Report and Written Opinion for Application No. PCT/US2015/040230 dated Oct. 22, 2015 (7 pages).

* cited by examiner

FIGURE 1
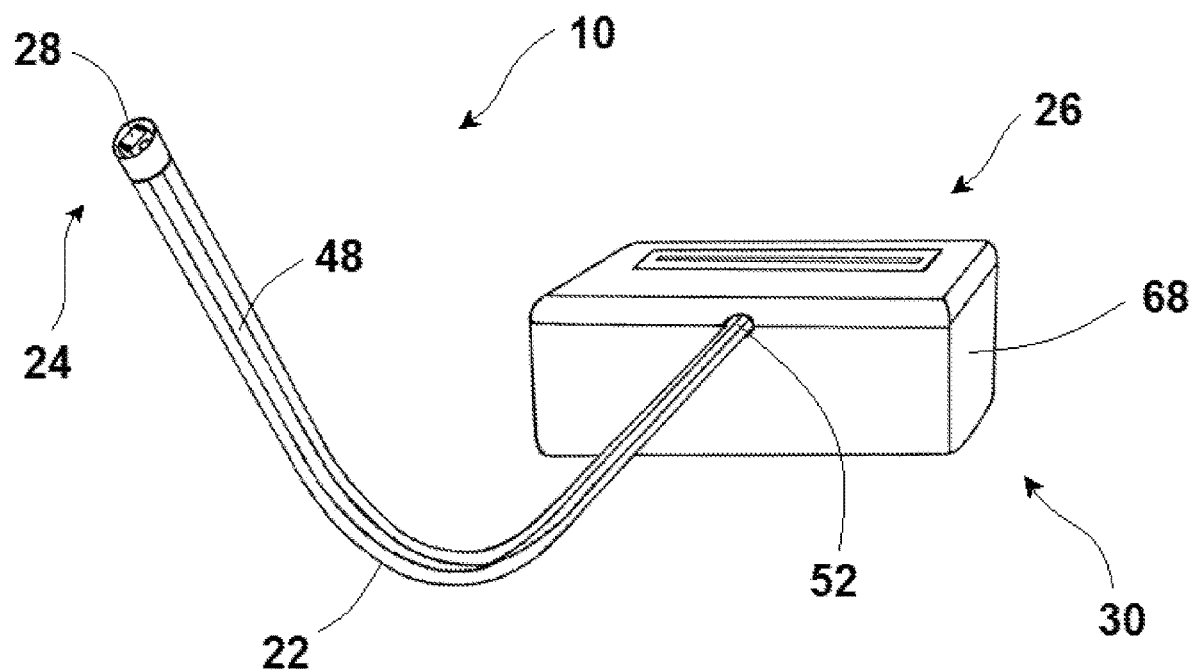
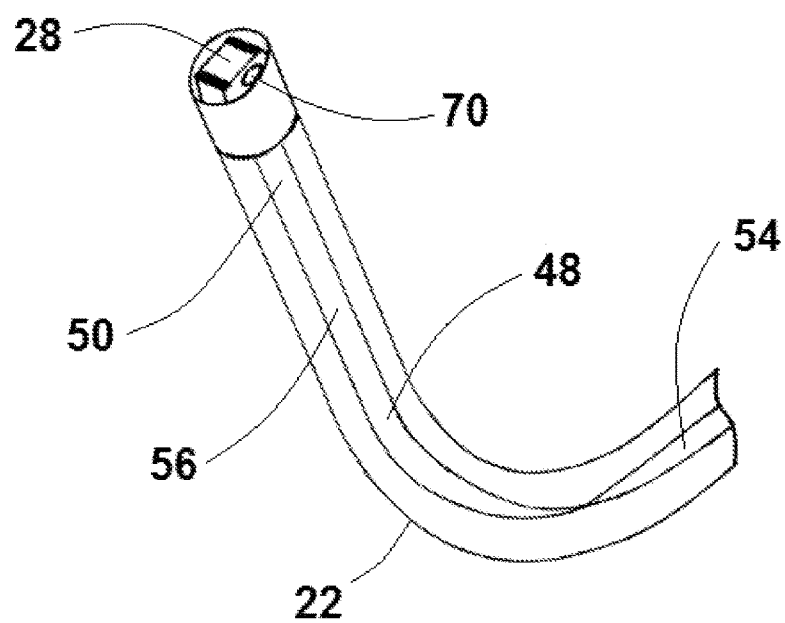
FIGURE 3

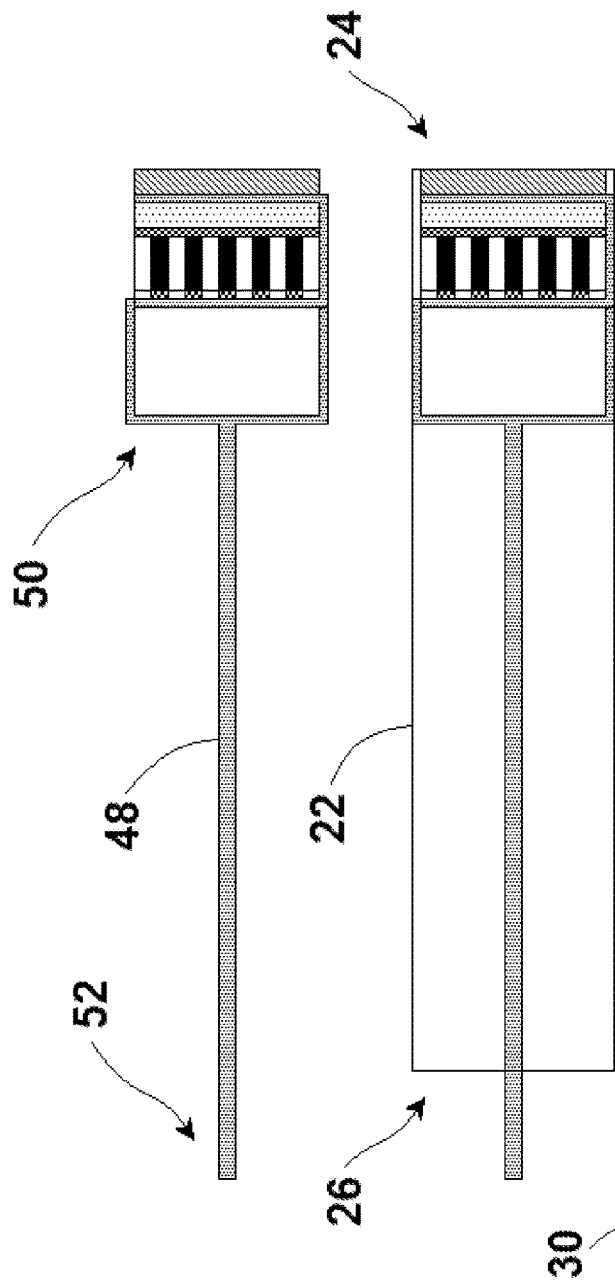
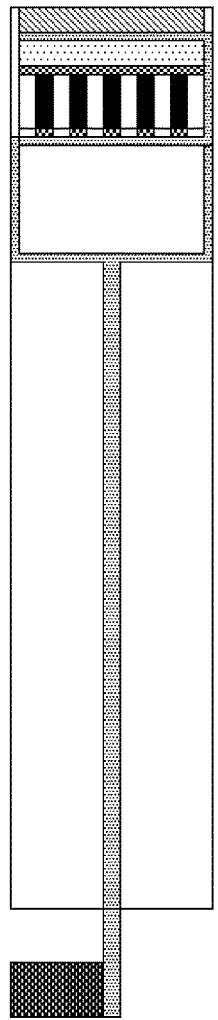
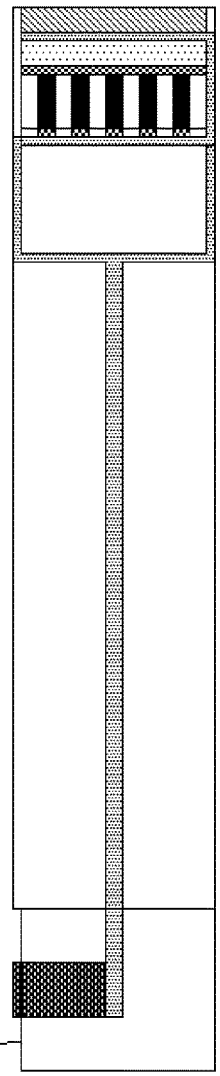
FIGURE 23
FIGURE 24
FIGURE 25
FIGURE 26

FORWARD-LOOKING ULTRASOUND ARRAY PROBE FOR INTRAVASCULAR IMAGING AND NAVIGATION APPLICATIONS

CROSS REFERENCE TO RELATED APPLICATION(S)

This is a U.S. national stage entry of International Patent Application No. PCT/US2015/040230, filed on Jul. 13, 2015, which claims priority to U.S. Provisional Patent Application No. 62/023,867, filed on Jul. 12, 2014, the entire contents of all of which are fully incorporated herein by reference.

This invention was made with government support under NIH/NIBIB Grant P41EB002182-16 awarded by the National Institutes of Health. The government has certain rights in the invention.

BACKGROUND OF THE INVENTION

1. Field of the Invention

The present invention generally relates to forward-looking ultrasonic imaging devices for use in medical procedures and methods of using and manufacturing those devices.

2. Description of Related Art

Atherosclerosis is a disease where plaque builds up inside arteries. Atherosclerosis remains the leading cause of morbidity and mortality in the developed world. In the United States, in men and women after 40, clinical manifestations of atherosclerosis occur in every 2 out of 3 men and 1 out of 2 women. W. Rosamond, et al., *American Heart Association Journals*, 2008.

When atherosclerosis manifests itself in the peripheral arteries (e.g., arteries in the legs and arms), the disease is called Peripheral Arterial Disease (PAD) sometimes also known as peripheral vascular disease (PVD). In the United States, it is estimated that 17.6 million people have PAD. Each year, 75,000 people die from PAD. Further, each year 100,000 people undergo leg amputation due to PAD making PAD the leading cause of leg amputation. Common sites for PAD are the iliac artery, femoral artery, popliteal artery and tibial artery, both anterior and posterior.

For intravascular treatment of PAD or atherosclerosis, it remains a challenge to navigate a diagnostic or therapy delivery device through the patient's vasculature. For example, a common current treatment to treat PAD or atherosclerosis is to use side-looking or oblique angle intravascular ultrasound (IVUS) to guide navigation of devices to diagnose, clear or punch through a blocked artery. For example, standard imaging IVUS catheters using piezoelectric transducers typically position the transducers at about forty-five degree angles to the linear axis of the catheter thereby providing conical but not truly forward-looking views. Of course, this limitation makes it difficult if not impossible to image an object directly in front of the catheter rather than along the sides.

For example, where an artery is completely blocked with plaque (a "chronic total occlusion" or CTO), of course there is a significant decrease in blood flow. But, without being able to see ahead of a diagnostic of therapy delivery device, it is difficult to maneuver to the site of the CTO and once there, diagnose the extent of the blockage or provide therapy when the only view the physician gets of the CTO is to the side and typically behind the CTO.

Various devices have been developed to produce forward-looking IVUS images. Most of these devices include locating mechanically moving piezoelectric transducers on the distal end of catheters and aiming the mechanism in a generally forward-looking direction. The transducers are then moved back and forth to "scan" the area in front of the catheter. These devices have been largely unsuccessful because of both the complexity of the mechanical mechanisms and the inability to create small enough arrays of piezoelectric transducers to allow the resulting catheter to be small enough to be able to be used in the relatively small arteries that comprise most of a patient's vasculature. For example, it is desirable for the cross-sectional diameter of coronary catheters to be less than 3F (1 mm). The cross-sectional area for devices used in the peripheral arteries can be larger. But, in any event, the cross-sectional diameter of any useful catheter is small thereby making it extremely difficult to design and produce transducers capable of producing strong forward-looking IVUS signals and then being able to receive the return echo ultrasonic signals and convert them to an electric signal that can be processed.

Although materials exist that allow such transducer arrays to be made small enough to make small-diameter devices, some of these materials in such small sizes do not produce adequate ultrasonic signals nor are sensitive enough to receive the return ultrasonic signals. Further, other promising materials have physical characteristics that make it extremely difficult to manufacture the necessary arrays or if such arrays can be made, lack durability in use to be practical. For example, PMN-PT is a material that is efficient at producing ultrasonic signals in response to electrical stimulation and also is good at picking up returning ultrasonic signals and converting them back to an electrical signal. But, PMN-PT is extremely brittle. As a result, it is therefore also extremely difficult to make it into a small multi element array.

In view of the foregoing, it is desirable to have a device for producing IVUS images directly in front of the device that eliminates these stated problems.

SUMMARY OF THE INVENTION

The present invention is an intraluminal forward-looking image producing device and associated methods of use and construction. In particular, the device of the present invention is an intraluminal forward-looking intravascular ultrasound (IVUS) image producing device. The invention also encompasses methods of using the intraluminal forward-looking intravascular ultrasound (IVUS) image producing device to image objects and material in a forward direction. The disclosed methods also involve manufacturing the intraluminal forward-looking intravascular ultrasound (IVUS) image producing device including the piezoelectric transducer. The resulting device is an elongated body configured to fit within the lumen of a vessel and having an imaging sensor located on the distal end of the elongated body configured to image objects and material in a forward direction. The method further involves inserting the intraluminal forward-looking intravascular ultrasound (IVUS) image producing device into a lumen of a vessel, and imaging objects or material in a forward direction. The methods of the present invention are particularly useful in vascular diagnostic and therapeutic procedures when the vessel has been completely blocked by plaque and imaging of the occlusion is required.

Unlike conventional imaging catheters that can only image objects to the side of the catheter or at best oblique angles, the present intraluminal forward-looking intravascular ultrasound (IVUS) image producing device produces images in a forward field of view. The ability to "see" in a forward direction is particularly useful for diagnosing and treating vascular diseases such as PAD and coronary artery disease. In particular, the present invention is particularly useful in treating blockages in blood vessels, particularly in the arteries. To accomplish this forward looking field of view, the imaging transducer is located on the distal end of the probe and directed in a forward direction.

There are many objects of the present invention in its various embodiments that may be addressed individually or in combinations and permutations. Each embodiment may address one or several of the following objectives.

An object of this invention in one embodiment or variant of the invention is to provide a forward-looking IVUS device that produces an image of what is directly in front of the device.

Another object of this invention in one embodiment or variant of the invention is to provide a forward-looking ultrasonic imaging transducer and corresponding device that can be used for imaging tissue without any moving parts.

Another object of this invention in one embodiment or variant of the invention is to provide a forward-looking ultrasonic imaging transducer and corresponding device that does not require significant electronics to be located on or very near the transducer.

These and other objects and advantages of the invention will be clear in view of the following description to the invention including the associated drawings.

BRIEF DESCRIPTION OF THE DRAWINGS

The invention will be described hereafter in detail with particular reference to the drawings. Throughout this description, like elements, in whatever embodiment described, refer to common elements wherever referred to and referenced by the same reference number. The characteristics, attributes, functions, interrelations ascribed to a particular element in one location apply to that element when referred to by the same reference number in another location unless specifically stated otherwise. All Figures are drawn for ease of explanation of the basic teachings of the present invention only; the extensions of the Figures with respect to number, position, relationship, and dimensions of the parts to form the preferred embodiment will be explained or will be within the skill of the art after the following description has been read and understood. Further, the exact dimensions and dimensional proportions to conform to specific force, weight, strength and similar requirements will likewise be within the skill of the art after the following description has been read and understood.

FIG. 1 is a perspective view of catheter of the present invention.

FIG. 3 is a close up view of the distal end of the catheter of FIG. 1.

FIG. 23 is a side schematic view of the assembly of FIG. 22 with the flexible circuit attached to the acoustic stack.

FIG. 24 is a side schematic view of the assembly of FIG. 23 with the flexible circuit previously attached to the composite array threaded down the catheter and with the acoustic stack positioned at the distal end of the catheter so that the guide-wire port just extends beyond the distal end of the catheter.

FIG. 25 is a side schematic view of the assembly of FIG. 24 with the traces and ground electrode of the flexible circuit soldered to the high-density interposer board for high-frequency applications or board-to-board connector.

FIG. 26 is a side schematic view of the assembly of FIG. 25 enclosed within a protective case.

DETAILED DESCRIPTION

A forward-looking ultrasound array probe of the invention is shown in FIG. 1 and is generally referred to as 10. "Forward-looking" means that probe 10 produces an image of what is in front of the distal end of the probe 10 (i.e., perpendicular to the axis of the probe 10 and away from the farthest end of the probe 10). The forward-looking probe 10 improves vessel navigation capability by providing healthcare practitioners with visual feedback that enables them to see where the distal end of the probe 10 is, what lies in front of the probe 10 and where the probe 10 is heading to in order to avoid unintended consequences such as poking the vessel wall. Further, the forward-looking probe 10 also can provide information about the nature or characteristics of tissue or other material in front of the probe 10.

Figure 2:
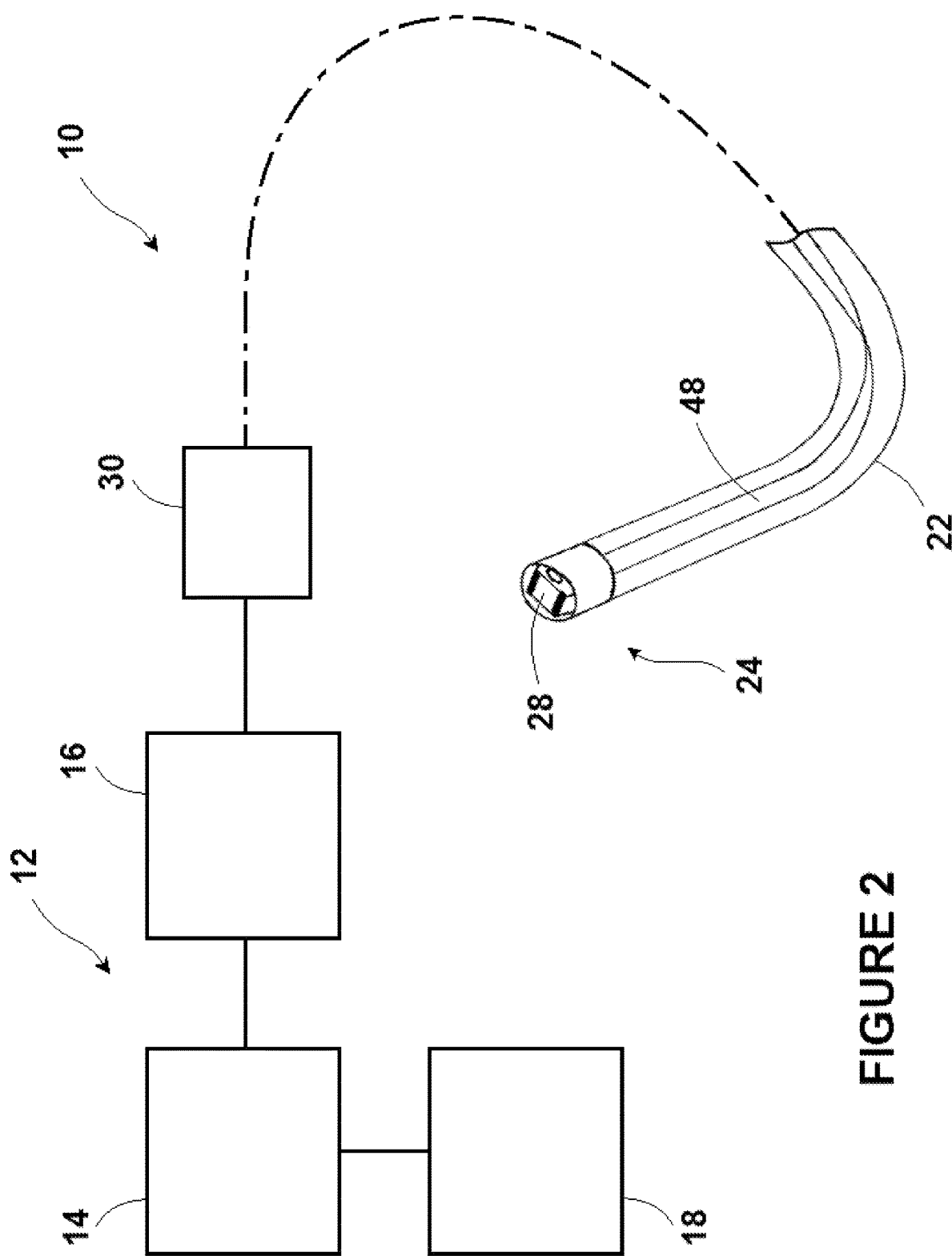
FIG. 2 is a schematic view of an IVUS system incorporating the catheter of FIG. 1.

The probe 10 of the present invention is intended to be used with an IVUS imaging system 12 such as that shown in FIG. 2. The imaging system 12 comprises the probe 10 coupled to an IVUS control system 14. Typically, the probe 10 is coupled to the IVUS control system 14 through a patient interface module (PIM) 16 that provides physical and electrical isolation between the probe 10 and IVUS control system 14 and may in addition provide control of the probe 10 or signal processing of the signal produced by the probe 10. The control system 14 is coupled to a monitor 18 for display of an IVUS image.

The control system 14 also prepares and sends electrical signals to the probe 10 to activate piezoelectric elements 20 to produce the ultrasonic signal that is sent from the elements 20 to the object or material being imaged. For example, the control system 14 controls the selection of particular transducer elements 20 to activate as well as the timing and duration of the electrical pulses sent to the elements 20. The control system also applies signal processing techniques including amplification, filtering, noise reduction and other well-known techniques to discriminate and enhance the received ultrasonic signal. Further the control system 14 includes beam forming processing to deconstruct the received ultrasonic signal to create an image of the tissue or material that produced the reflected ultrasonic signal which image is displayed on the monitor 18.

The forward-looking ultrasound array probe 10 in a preferred embodiment shown in FIG. 1 has the following basic elements: a medical grade polymer protective catheter 22 having a distal end 24 and a proximal end 26 and an acoustic stack 28 located at the distal end 24 that is electrically connected to an imaging system connection 30.

The acoustic stack 28 is an ultrasound imaging assembly that includes an imaging surface 32. Ultrasonic signals are both produced and received by the imaging surface 32. The imaging surface 32 is aimed in a direction aligned with the axis of the catheter 22 and distal to the distal end 24, to produce imaging data from objects or material in front of the imaging surface 32. The imaging surface 32 is primarily comprised of a piezoelectric ceramic/polymer composite array 34 having a front side 36 and a back side 38. Optimally, the piezoelectric ceramic/polymer composite array 34 has determined dimensions in the horizontal and vertical directions, referred to as azimuth and elevation apertures, respectively, as will be described hereafter.

Piezoelectric transducers, such as the piezoelectric ceramic/polymer composite array 34, translate electrical energy into ultrasonic energy, with is emitted, and then translates ultrasonic energy received after being reflected back by objects or material into electrical energy. The effectiveness of these translations depends largely on the material chosen, the dimensions of the transducer and its components and the type and dimensions of the coating materials, all taken as a whole. Because the transducer is a three dimensional electro-mechanical device, it is capable of operating in several possible resonate modes with one or more modes dominating. Ideally, a transducer is designed in material, dimensions and coatings to create, at a desired frequency or within a desired frequency range, a single dominate mode suppressing all other modes as "spurious."

The most common method used to design a transducer with a single dominate mode of operation is to create a single "port" or "window" to the medium outside of the transducer (e.g., blood). The single port is created by mounting the transducer, in this case the piezoelectric ceramic/polymer composite array 34, so that the most efficient resonant mode of the transducer faces the port, which in this case is the open distal end 24 of catheter 22, with all other modes suppressed by means of mechanical dispersion. This mechanical dispersion is accomplished by the choice of transducer dimensions and the matching layers which have a dampening effect.

The preferred material for the piezoelectric ceramic/polymer composite array 34 is single crystal PMN-PT such as that made by CTG Advanced Materials (formerly H.C. Materials Corporation) of Bolingbrook, Ill., USA. This material is ideal for this application due to its high dielectric constant and low dielectric loss. These properties make it ideal for high sensitivity transducers with small-aperture size such as is required by the present probe 10. Although piezoelectric ceramic/polymer composite array 34 is preferably made of lead magnesium niobate-lead titanate (PMN-PT), other similar piezoelectric material may be used including, but not limited to, lead zirconate niobate-lead titanate (PZN-PT), lead zirconate titanate (PZT), lead indium niobate-lead magnesium niobate-lead titanate PIN-PMN-PT, manganese-doped PMN-PT (Mn:PMN) and manganese-doped PIN-PMN-PT.

Ideally, the present invention is intended to be operated at frequencies between about 9 MHz to about 45 MHz, more preferably at frequencies between about 20 to about 40 MHz and ideally operated at a frequency of about 30 MHz. In this frequency range, the images produced by the invention will have good resolution, penetrate tissue (e.g., blood vessel wall) or obstructions (e.g., plaque) enough to produce good information about this material and not be blinded by blood speckle that is typically found at higher frequencies. Although the ideal operating range of the present invention is between 20-40 MHz, the invention may be operated at higher or lower frequencies.

The front side 36 of the piezoelectric ceramic/polymer composite array 34, with certain coatings as will be described hereafter, is the imaging surface 32. The front side 36 is preferably uniformly metal-sputtered so that one or more conductive matching layers can be bound to the front side 36 as will be described hereafter.

Figure 6:
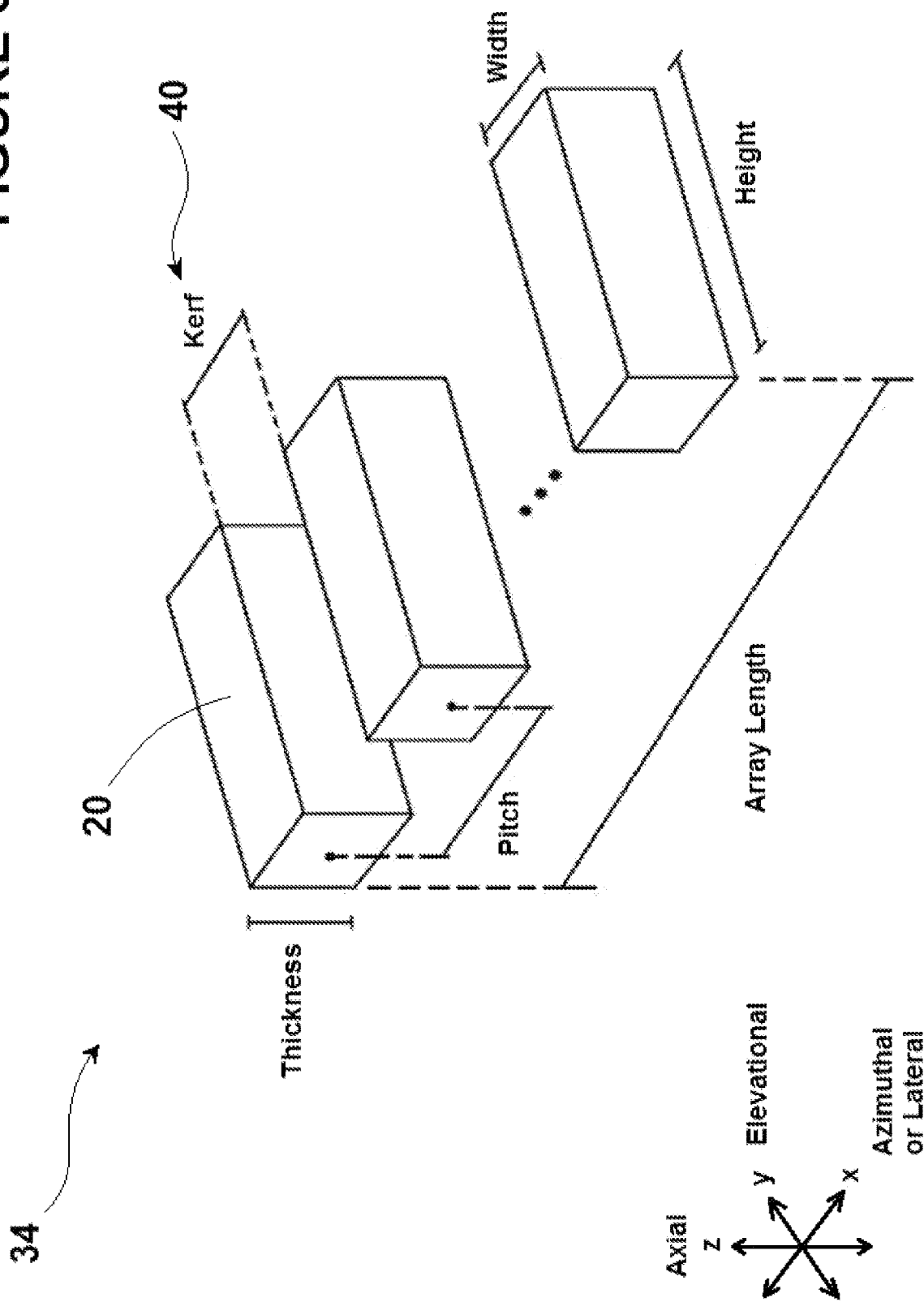
FIG. 6 is a perspective schematic view of the configuration of the piezoelectric ceramic/polymer composite array of the invention of FIG. 1.

In a preferred embodiment illustrated in FIG. 6, the piezoelectric ceramic/polymer composite array 34 has a determined number of piezoelectric ceramic elements 20 and polymer filled kerfs 40 spaced at a determined optimal pitch (i.e., separation between the center of adjacent elements 20) for the suppression of grating lobes that could ultimately affect the quality of the produced ultrasound images. In a preferred embodiment of the probe 10, the number of elements 20 is 32, the width of each element 20 is 19 µm, the spacing of kerfs 40 is 6 µm and the pitch ($0.5\lambda_{water}$) is 25 µm. As a result, this preferred embodiment of the piezoelectric ceramic/polymer composite array 34 has a height of about 1 mm and a length of about 0.8 mm. The number of elements 20 and the dimensions given are representative and not limiting. More or less elements 20 may be used and the dimensions may be varied and still be within the scope of the invention.

Figure 5:
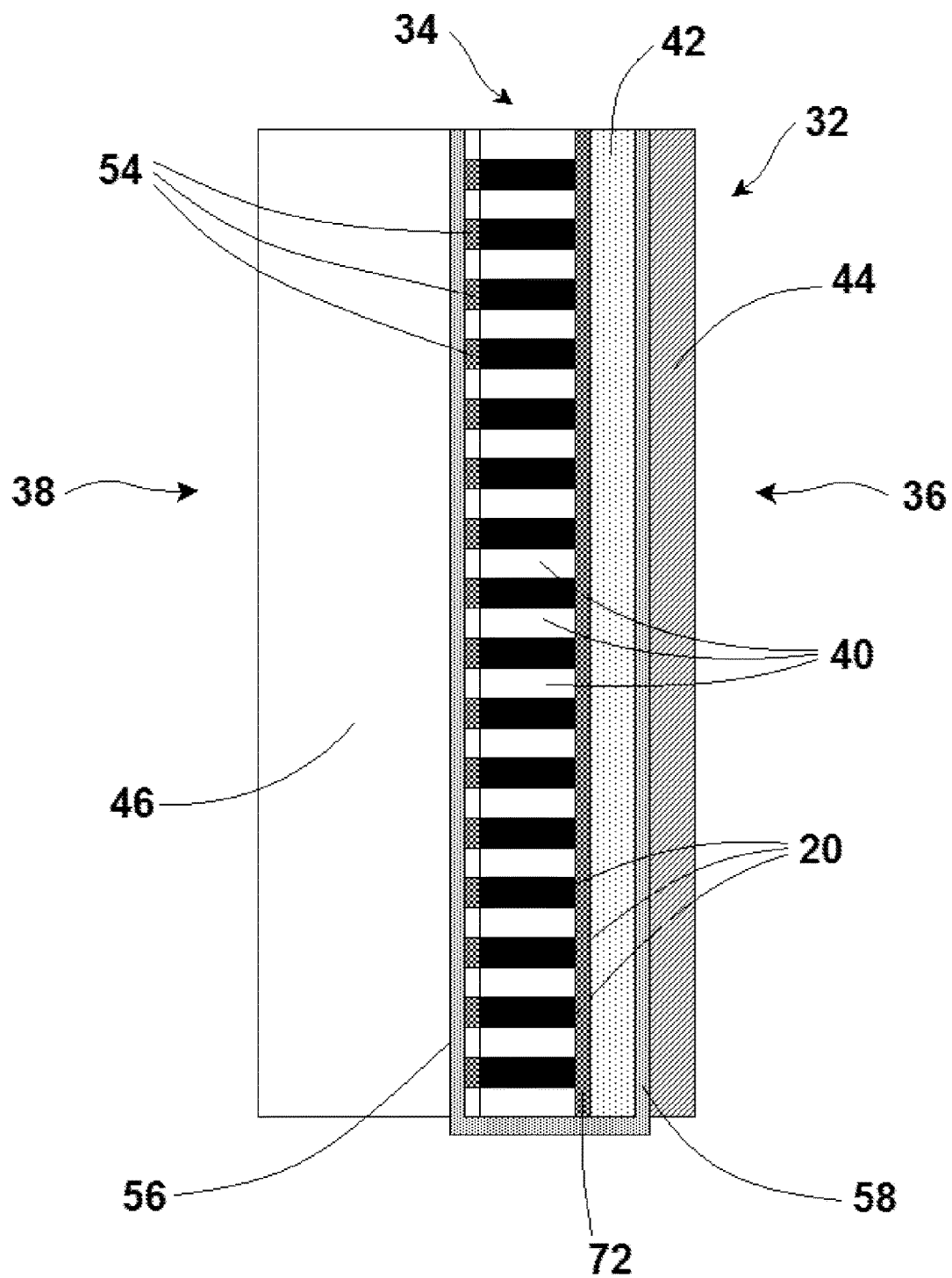
FIG. 5 is a side view of the acoustic stack of the invention of FIG. 1.

As mentioned above, the piezoelectric ceramic/polymer composite array 34 additionally has a conductive matching layer, first front side matching layer 42, that is made of an electrically conductive mixture of metallic powder with polymer. (FIG. 5) The function of this first front side matching layer 42 is to provide efficient transmission of sound waves from the transducer elements 20 to the ambient environment (e.g., blood). To prepare the piezoelectric ceramic/polymer composite array 34 to receive the first front side matching layer 42 and to form a common ground electrode 72, the front side 36 of the piezoelectric ceramic/polymer composite array 34 is coated with a layer of metal. The metal used to coat the front side 36 is preferably a combination of chrome and gold, although any metal including but not limited to, titanium, tin, zinc, and silver, can also be used. The metal coating is preferably done by sputtering as is well understood by those skilled in the art.

In a preferred embodiment of the probe 10, the first front side matching layer 42 is a 2-3 µm silver epoxy sold by the Aldrich Chemical Company of St. Louis, Mo., USA that is applied to be about 25 µm thick and has a resulting acoustic impedance of about between 7 and 15 MRayls. First front side matching layer 42 is individually fabricated as described below and then bonded together to the metal-sputtered front side 36 of the piezoelectric ceramic/polymer composite array 34 using unloaded epoxy. The preferred material for the bonding material is Insulcast 501 sold by American Safety Technologies of Montgomeryville, Pa., USA although any other similar material may be used.

As mentioned, the first front side matching layer 42 is preferably made of 2-3 µm Silver Epoxy that is preferably about 25 µm thick and has a resulting acoustic impedance of about between 7 and 15 MRayls. But, any other material that accomplishes the function of first front side matching layer 42 can also be used in the invention. Examples of such material include, but are not limited to, epoxy, epoxy filled with one or more different fillers such as metal-impregnated graphite, glass ceramic, composite ceramic and metal (including, but not limited to, copper, copper alloy, copper with graphite pattern embedded therein, magnesium, magnesium alloy, aluminum, aluminum alloy and gold). The particular filler used may be specifically chosen to adjust the acoustic impedance of the first front side matching layer 42.

In a preferred embodiment of the probe 10, the epoxy used to bond the first front side matching layer 42 to the front side 36 is Epotek 301 epoxy sold by Epoxy Technology of Billerica, Mass., USA. Although Epotek 301 has been described as the preferred bonding material for bonding the first front side matching layer 42 to the front side 36, any bonding material that is able to bond the conductive first front side matching layer 42 to the metal-sputtered front side 36 and preserve electrical conductivity between the first front side matching layer 42 and front side 36 and that is biocompatible may be used as will be clear to those skilled in the art. Although Epotek 301 has been described as the preferred material for bonding the first front side matching layer 42 to the front side 36, any other material that accomplishes this function can also be used in the invention.

In addition to the conductive first front side matching layer 42, the acoustic stack 28 also includes a second front side matching layer 44 that overlays and seals the first front side matching layer 42 as the acoustic stack 28 is located in and affixed to the distal end 24 of the catheter 22 as will be explained hereafter. (FIG. 5) The second front side matching layer 44 is preferably Parylene C sold by Specialty Coating Systems Inc. of Indianapolis, Ind., USA. This second front side matching layer 44 is preferably vapor deposited on the first front side matching layer 42, as is well understood in the art, in a thickness of 15 µm. In addition to aiding in the acoustic matching of the piezoelectric ceramic/polymer composite array 34 to the ambient environment (e.g., blood), another purpose of the second front side matching layer 44 is to seal the distal end 24 of the catheter 22 when the acoustic stack 28 is located at the distal end 24 of the catheter 22.

Further, the first front side matching layer 42 individually may have any thickness and the first front side matching layer 42 and second front side matching layer 44 together may have any combined thickness. A preferred thickness of the first front side matching layer 42 is approximately ¼ or less of the wavelength at the resonant frequency of the piezoelectric ceramic/polymer composite array 34. But, the first front side matching layer 42 may be more than approximately ¼ of the wavelength at the resonant frequency of the piezoelectric ceramic/polymer composite array 34. For example, the combined thickness of the first front side matching layer 42 and the second front side matching layer 44 may be approximately ½ of the wavelength at the resonant frequency of the piezoelectric ceramic/polymer composite array 34. Further, in some embodiments of the probe 10, either the first front side matching layer 42 or the second front side matching layer 44 may be approximately ¼ of the desired wavelength or less in order to minimize destructive interference caused by ultrasonic waves reflected from the boundaries between the first front side matching layer 42 and the second front side matching layer 44.

The piezoelectric ceramic/polymer composite array 34 also includes a non-conductive backing layer 46 that is located on the back side 38 of the piezoelectric ceramic/polymer composite array 34. (FIG. 5) The function of the non-conductive backing layer 46 is to avoid reverberation or ringing of the piezoelectric ceramic/polymer composite array 34. In a preferred embodiment of the probe 10, non-conductive backing layer 46 is also Epotek 301 epoxy. Although Epotek 301 epoxy is the preferred material for the non-conductive backing layer 46, any material that performs the function of the non-conductive backing layer 46 may be used.

The acoustic stack 28 is enclosed in and mounted to a catheter 22 at the distal end 24 of the catheter 22. (FIG. 3) The body of the catheter 22 is preferably made by conventional extrusion techniques as are well understood in the art. The materials used to extrude the body of the catheter 22 are typically organic polymers including, but not limited to, polyesters, polyvinylchloride, polyurethanes, polytetrafluoroethylenes (PTFE), silicone rubbers, natural rubbers and similar biocompatible materials. The body of the catheter 22 may also be reinforced to increase rotational and column strength, toughness, pushability and other mechanical properties of the catheter 22. For example, the body of the catheter 22 may be reinforced with braid, coils, helical wires, axial filaments or a combination of these.

As mentioned, the body of the catheter 22 may be formed by extrusion. As a result, the catheter diameter can easily be selected. The catheter 22 in a preferred embodiment is a 6F catheter (2 mm diameter). Although the catheter 22 has been described as having a 6F diameter, any diameter can be used suitable for the intended use, as will be clear to those skilled in the art, may be used according to the teachings of the present invention. Further, the catheter 22 has a length that allows the catheter 22 to be admitted into a patient's artery and advanced to a desired location as is well understood in the art.

The combination of materials chosen, thickness of the material and whether reinforcing material is used affects the flexibility of the resulting catheter 22. The materials should be selected to provide a biocompatible catheter 22 with sufficient flexibility to pass through the desired arteries and with sufficient stiffness to allow the catheter 22 to be pushed through the arteries to a desired location.

Figure 4:
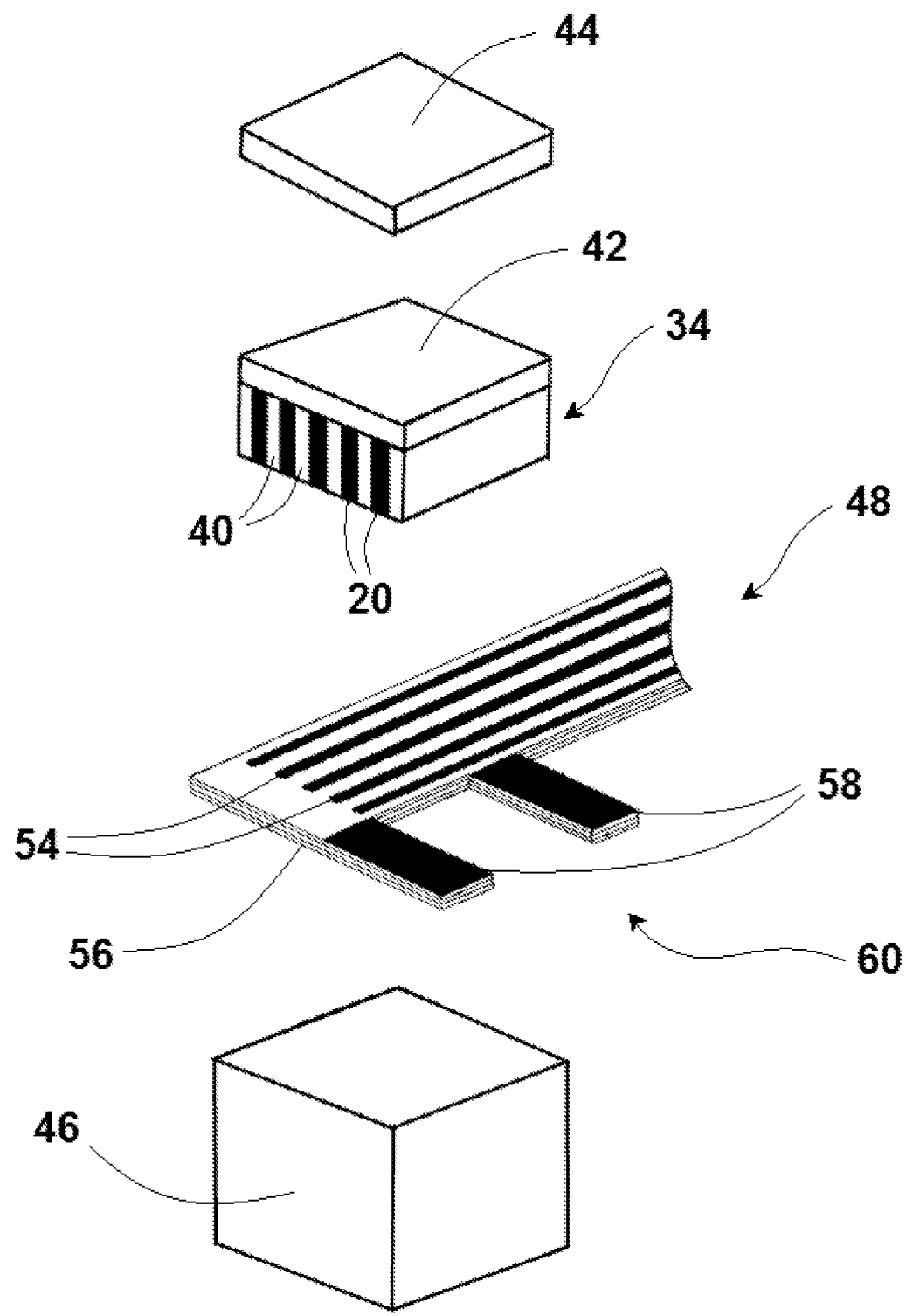
FIG. 4 is an exploded view of the acoustic stack of the invention of FIG. 1.

A multi-layer flexible circuit 48 electrically connects the piezoelectric ceramic/polymer composite array 34 to the imaging system connection 30. (FIG. 1) The multi-layer flexible circuit 48 has a distal end 50 and a proximal end 52. The multi-layer flexible circuit 48 has a series of signal carrying traces 54 (FIG. 4) and a ground electrode 56 all of which extend from the distal end 50 to the proximal end 52 of the multi-layer flexible circuit 48. The ground electrode 56 terminates at its distal end 50 in projecting flaps 58 that form a grounding clamp 60. (FIG. 4)

The distal end 50 of the multi-layer flexible circuit 48 is bonded together to the piezoelectric ceramic/polymer composite array 34 using unloaded epoxy, aligning the metal-sputtered piezoelectric ceramic elements 20 with the metallic transmission/reception traces 54 on the multi-layer flexible circuit 48. The preferred unloaded epoxy used in the preferred embodiment of the probe 10 to bond the distal end 50 of the multi-layer flexible circuit 48 to the back side 38 of the piezoelectric ceramic/polymer composite array 34 is Epotek 301. Although Epotek 301 has been described as the preferred bonding material for bonding the distal end 50 of the multi-layer flexible circuit 48 to the back side 38 of the piezoelectric ceramic/polymer composite array 34, any bonding material that is able to securely attach the distal end 50 of the multi-layer flexible circuit 48 to the back side 38 of the piezoelectric ceramic/polymer composite array 34 and that is biocompatible may be used as will be clear to those skilled in the art.

The projecting flaps 58 that form grounding clamp 60 embrace the piezoelectric ceramic/polymer composite array 34 and the first front side matching layer 42 with the purpose of holding these two components in place and electrically connecting the front side 36 of the first front side matching layer 42 to the ground electrode 56 of the multi-layer flexible circuit 48. (FIG. 4)

The acoustic stack 28 and the multi-layer flexible circuit 48 are placed inside the medical grade polymer protective catheter 22, and the acoustic stack 28 is fixed to one end of the medical grade polymer protective catheter 22 using unloaded epoxy, leaving space for a guide-wire port 70 as will be described hereafter. (FIG. 3) The distal end 24 of the medical grade polymer protective catheter 22 having the acoustic stack 28 is covered with the second front side matching layer 44 made of biocompatible, electrically non-conductive polymer preferably by vapor deposition.

The proximal end 52 of the multi-layer flexible circuit 48 is electrically connected to an imaging system connection 30. (FIGS. 7 and 8) The imaging system connection 30 connects the probe 10 to the IVUS imaging system 12. (FIG. 2) As can be seen, with this configuration, there are no electronics located at or near the piezoelectric ceramic/polymer composite array 34 such as is the case with existing IVUS devices. Because there are no on-site electronics, there are no electronics to make space for thus decreasing the dimensions needed to house and accommodate the piezoelectric ceramic/polymer composite array 34. This allows a smaller diameter probe 10 to be made than is presently available.

Figure 7:
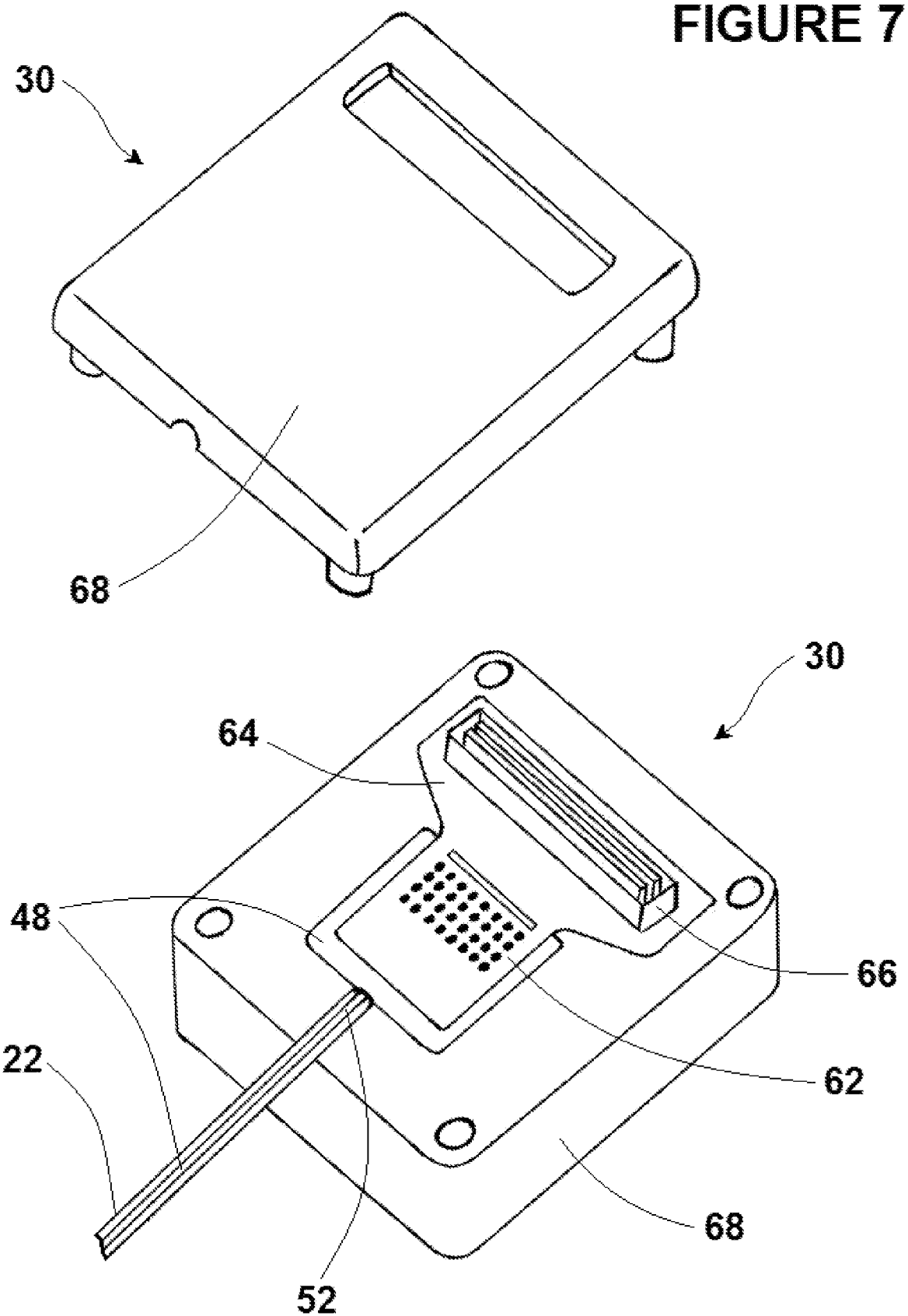
FIG. 7 is a perspective exploded view of one embodiment of the proximal end of the catheter of FIG. 1.

In an embodiment of the probe 10 shown in FIG. 7, the imaging system connection 30 includes a high-density interposer board for high-frequency applications 62, a printed circuit board 64 and a board-to-board connector 66. The function of the high-density interposer board for high-frequency applications 62 is to save space on boards involving large arrays, minimizing stress on mating boards, reducing self-inductance, and reducing cross talk among the electrical signals being conveyed by the incoming signal carrying traces 54 of the proximal end 52 of the multi-layer flexible circuit 48. The function of the printed circuit board 64 is to convey the electrical signals from the high-density interposer board for high-frequency applications 62 to the board-to-board connector 66. The high-density interposer board for high-frequency applications 62 is electrically connected to the printed circuit board 64, and the printed circuit board 64 is electrically connected to the board-to-board connector 66. The imaging system connection 30 is enclosed within a polymer protective case 68 which contains and protects the imaging system connection 30.

Figure 8:
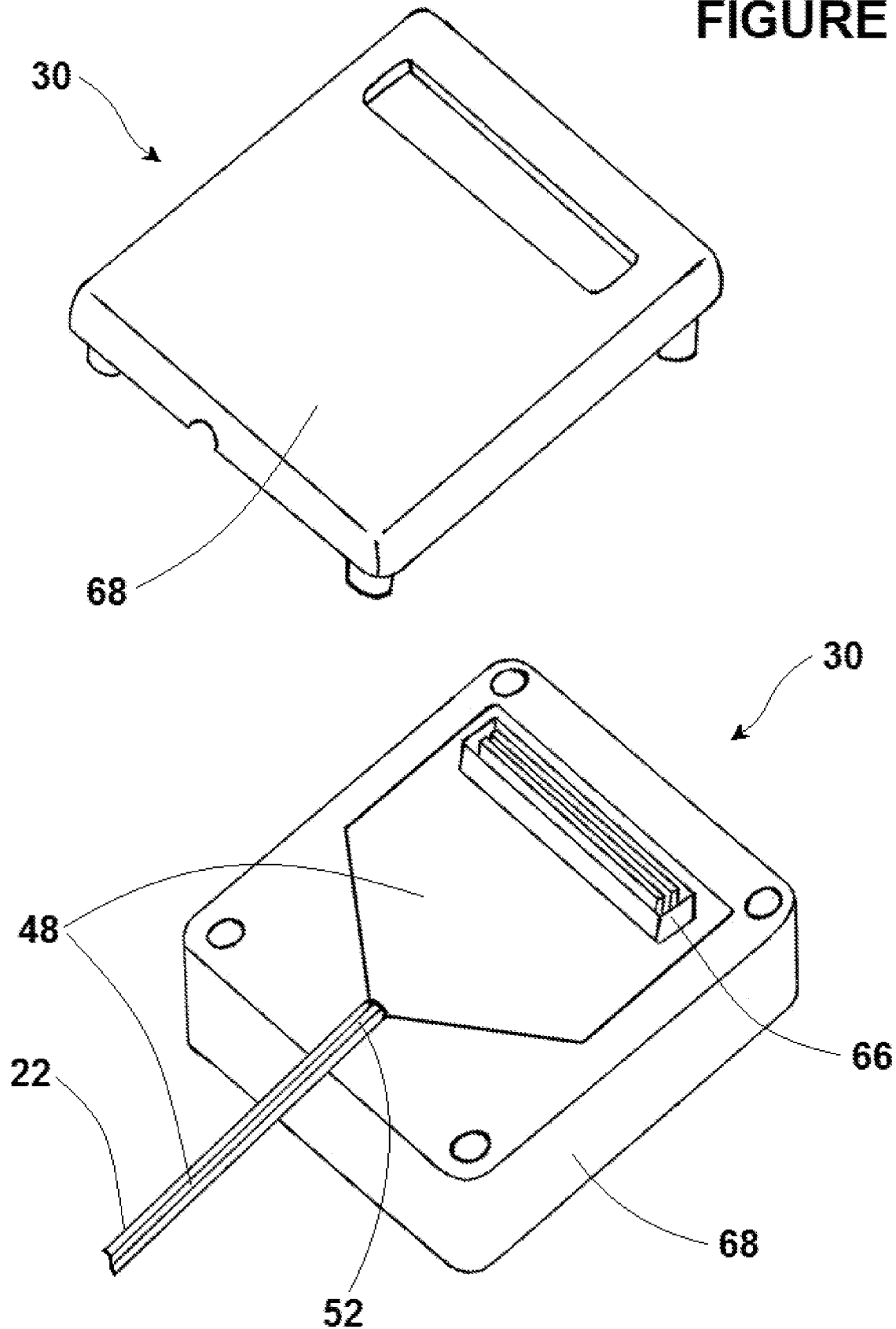
FIG. 8 is a perspective exploded view of another embodiment of the proximal end of the catheter of FIG. 1.

In another preferred embodiment of the imaging system connection 30 shown in FIG. 8, the board-to-board connector 66 is bonded directly to the flexible circuit 48. As a result, in this embodiment, there is no printed circuit board 64 or high-density interposer board for high-frequency applications 62. Consequently, the signal created by the returned ultrasound signal on the piezoelectric ceramic/polymer composite array 34 is transferred directly to the control system 14 through the interconnection of the imaging system connection 30 and the IVUS control system 14.

The probe 10 also preferably contains a guide-wire port 70 located at the distal end 24 of the catheter 22. (FIG. 3) The guide-wire port 70 allows the probe 10 to be inserted over a guide-wire in a well-known rapid-exchange configuration so that the probe 10 can easily be moved to a desired location in the patient's vasculature over an already-placed guide-wire as is well understood in the art. Although the probe 10 has been described as including a catheter 22 that is moved into position in an artery by moving over a guide-wire, the probe 10 may also not include the guide-wire port 70 so that the probe 10 is self-locating. "Self-locating" means that the probe 10 is moved to a desired location in a patient's vasculature (e.g., arteries) by manipulating the probe 10 itself. In a variant of this, if the probe 10 is made sufficiently small in diameter, the probe 10 itself can be a guide-wire that may be used to help position other devices as is common for such guide-wires.

The design described herein produces a probe 10 that has a natural focus 3.2 mm in front of the piezoelectric ceramic/polymer composite array 34. Further, because the piezoelectric ceramic/polymer composite array 34 is controlled by the IVUS control system 14, the resulting imaging beam can be steered (i.e., aimed) electronically without the need for moving or mechanical parts.

Functionally, the elements 20 are connected, via the traces 54 on the flexible circuit 48, to a generator in the IVUS control system 14 that transmits pulses of electricity to the elements 20. The electric pulses cause the piezoelectric element 20 of piezoelectric ceramic/polymer composite array 34 to contract and expand which produces mechanical oscillations in the piezoelectric element. These mechanical oscillations generate an acoustic signal, in this case, an ultrasonic signal. Thus, the piezoelectric element is essentially an electric-to-acoustic transducer.

To produce an image using the catheter 22 of the present invention, electrical signals are sent from the IVUS control system 14 to the probe 10 via the imaging system connection 30. The electrical signals travel through the traces 54 of the flex circuit 48 to activate selected piezoelectric elements 20. In response to the electrical signal, selected piezoelectric elements oscillate producing ultrasonic signals. The ultrasonic signals are emitted in a direction distal to the distal end 24 of the catheter 22 where they impinge on tissue, materials and objects that reflect a portion of the ultrasonic signal.

These reflected ultrasonic signals contact the elements 20 and induce and electric signal in response to the received ultrasonic signal. The induced electric signal is passed to the traces 54 where the electronic signal is passed to either the to the high-density interposer board for high-frequency applications 62 or board-to-board connector 66 prior to being sent to the IVUS control system 14 to be evaluated and turned into an IVUS image to be displayed on a monitor 18.

The IVUS control system 14 can control the operation of the piezoelectric ceramic/polymer composite array 34 so that the piezoelectric ceramic/polymer composite array 34 can operate in several modes. For example, the IVUS control system 14 can fire one element 20 and also receive the reflected ultrasound signal on the same element 20. Alternately, several elements 20 may be fired simultaneously and the reflected ultrasound signal can be received on the same or a subgroup of the elements 20 that created the ultrasound signal or on one of more different elements 20. Further, all the elements 20 can be fired simultaneously and the reflected signal can be received by all the elements 20.

Figure 9:
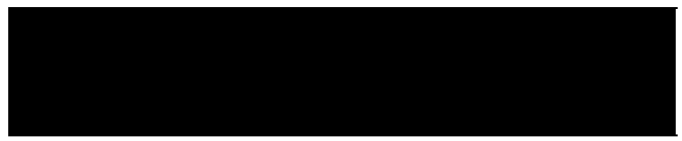
FIG. 9 is a side schematic view of a blank of piezoelectric material.
Figure 10:
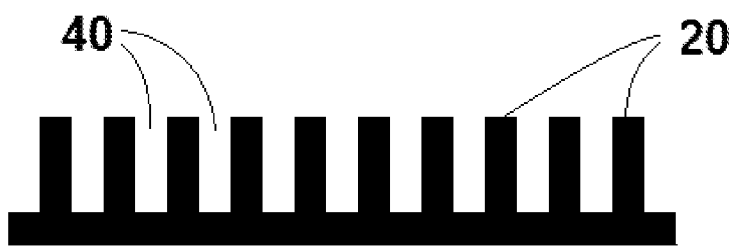
FIG. 10 is a side schematic view of blank of piezoelectric material of FIG. 9 with etchings performed according to a DRIE process to produce elements and kerfs.
Figure 11:
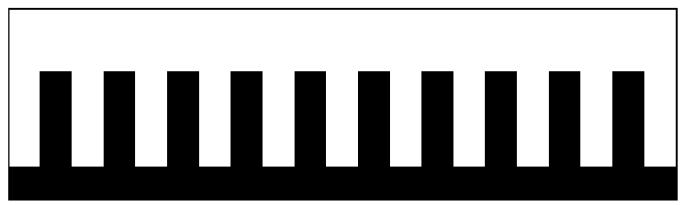
FIG. 11 is a side schematic view of assembly of FIG. 10 with the kerfs filled with a non-conducting material.

The process to fabricate the piezoelectric ceramic/polymer composite array 34 is shown in FIGS. 9-26 and described as follows. A blank of PMN-PT material is obtained having a thickness of about 27 μm. (FIG. 9) Although the preferred thickness of the PMN-PT material is about 27 μm, the thickness can range from about 25 to about 500 μm. The bulk PMN-PT material is polished and a nickel pattern mask is applied for the Deep Reactive Ion Etching (DRIE) process.

The DRIE process is performed, as is well understood in the art, to etch the kerfs 40 between the elements 20. (FIG. 10) The DRIE process preferably produces elements 20 having a 19 μm width, 1 mm height with a 6 μm wide kerf 40. Although the preferred method of producing elements 20 is by the DRIE process, any known process for producing such elements 20 may be used, as is well understood in the art, including but not limited to Reactive Ion Etching (RIE), laser etching, plasma etching, wet etching and photolithography.

The kerfs 40 are then filled with a non-conducting material 74. (FIG. 11) In the preferred embodiment, this non-conducting material 74 is Epotek-301 epoxy sold by Epoxy Technology of Billerica, Mass., USA although any appropriate biocompatible non-conducting material, as is well understood in the art, will work.

Figure 12:
FIG. 12 is a side schematic view of the assembly of FIG. 11 lapped down to expose the kerfs.
Figure 13:
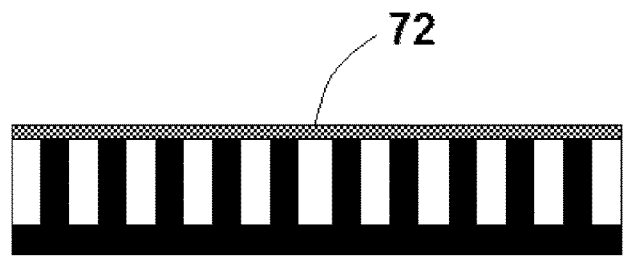
FIG. 13 is a side schematic view of the assembly of FIG. 12 with a common ground electrode formed on the front side of the array.
Figure 14:
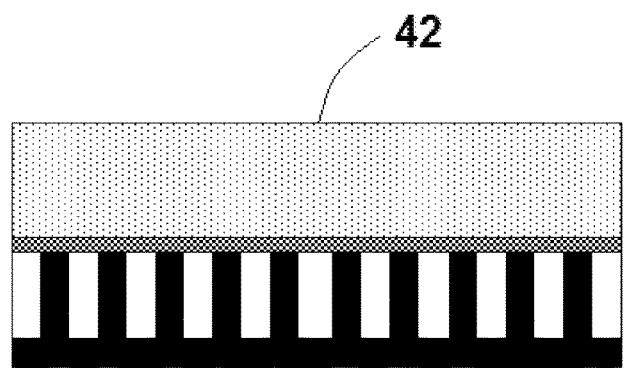
FIG. 14 is a side schematic view of the assembly of FIG. 13 with a first front side matching layer added to cover the array.

The DRIE cut piezoelectric ceramic/polymer composite array 34 with filled kerfs is lapped down, as is well understood in the art, to expose the kerfs 40 (FIG. 12).

Figure 15:
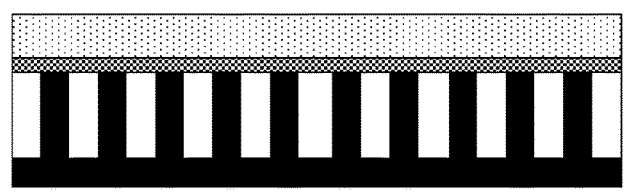
FIG. 15 is a side schematic view of the assembly of FIG. 14 with the first front side matching layer and bonding material lapped down to a final thickness.

A common ground electrode 72 is formed on the front side 36 of the ceramic/polymer composite array 34 by sputtering chrome and gold on to the front side as is well understood in the art. (FIG. 13) A first front side matching layer 42 is added to cover the piezoelectric ceramic/polymer composite array 34. (FIG. 14) The first front side matching layer 42 is formed by casting the conductive material of the first front side matching layer 42 with a bonding material, both as described above, around the front side 36 of the piezoelectric ceramic/polymer composite array 34. The first front side matching layer 42 made of 2-3 μm silver epoxy and Insulcast 501 is preferably lapped down to a final thickness of 25 μm. (FIG. 15)

Figure 16:
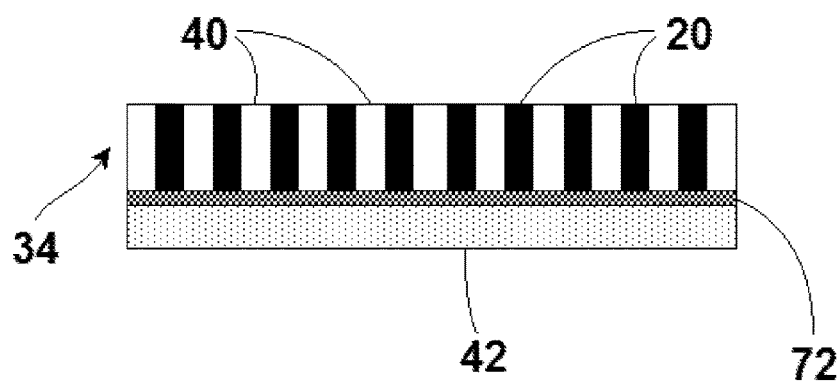
FIG. 16 is a side schematic view of the assembly of FIG. 15 with the assembly flipped over and lapped down to final thickness.
Figure 17:
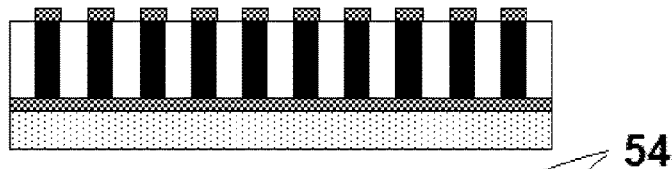
FIG. 17 is a side schematic view of the assembly of FIG. 16 with the individual connections to the elements formed.
Figure 18:
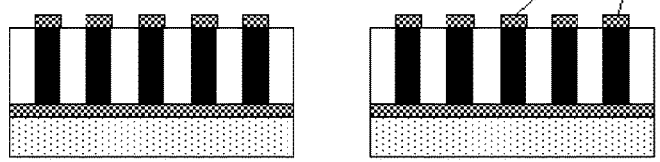
FIG. 18 is a side schematic view of the assembly of FIG. 17 with the individual arrays diced out.
Figure 19:
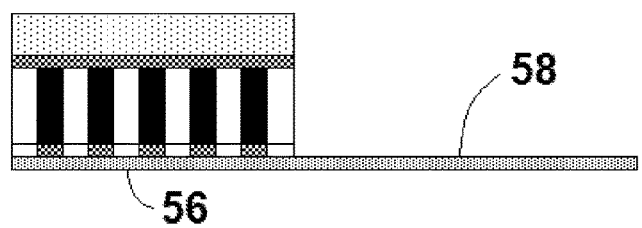
FIG. 19 is a side schematic view of the assembly of FIG. 18 with the individual arrays made up of elements and kerfs removed and bonded to the flexible circuit so that the individual signal traces of the flexible circuit are bonded to the respective individual elements.

The intermediate piezoelectric ceramic/polymer composite array 34, now composed of a DRIE cut layer of PMN-PT with kerfs 40 filled with Epotek-301 epoxy and a first front side matching layer 42 is then flipped over and lapped down to final thickness (27 μm of just PMN-PT composite or 52 μm which is the thickness of the PMN-PT composite array 34 and the first front side matching layer 42). (FIG. 16)

Figure 20:
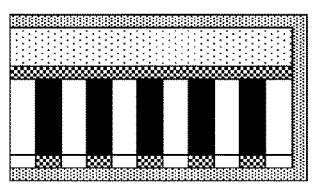
FIG. 20 is a side schematic view of the assembly of FIG. 19 with the ground flaps projecting flaps bent and bonded to the first front side matching layer to connect the first front side matching layer to the ground electrode of the flexible circuit.
Figure 21:
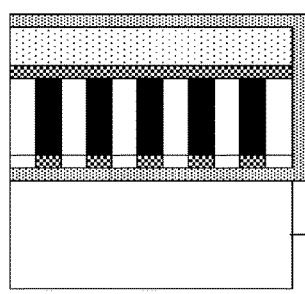
FIG. 21 is a side schematic view of the assembly of FIG. 20 with a backing layer made of a non-conducting material bonded to the ground electrode on the backside of the flexible circuit.
Figure 22:
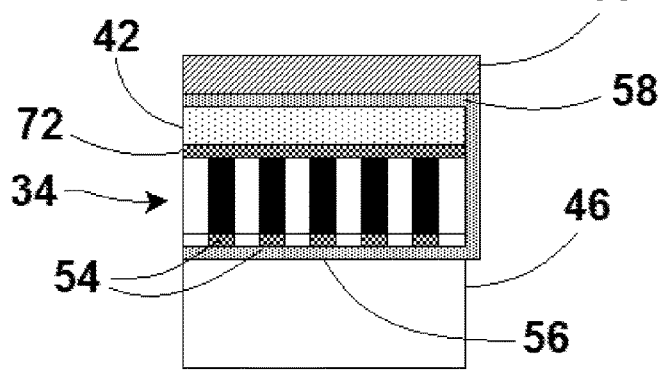
FIG. 22 is a side schematic view of the assembly of FIG. 21 with a second front side matching layer applied to the front side of the composite array.

The individual connections to the elements 20 that will be connected to the traces 54 are now formed. This is preferably done by sputtering metal to form the individual connections to the elements 20 within a pattern as is well understood in the art. (FIG. 17) The individual arrays made up of elements 20 and kerfs 40 are then diced out and the elements 20 are now formed. (FIG. 18) Once the individual arrays have been diced out, the individual arrays made up of elements 20 and kerfs 40 are removed and bonded to the flexible circuit 48 so that the individual signal traces 54 of the flexible circuit 48 can be bonded to the respective individual elements 20. (FIG. 19) The ground flaps projecting flaps 58 are then bent and bonded to the first front side matching layer 42 to connect the first front side matching layer 42 to the ground electrode 56 of the flexible circuit 48. (FIG. 20)

A backing layer 46, made of a non-conducting material, is then bonded to the ground electrode 56 on the backside of the flexible circuit 48. (FIG. 21) In the preferred embodiment, the backing layer 46 is made of Epotek-301 epoxy sold by Epoxy Technology of Billerica, Mass., USA and preferably has a thickness of <5 mm.

A second front side matching layer 44 is applied to the front side 36 of the piezoelectric ceramic/polymer composite array 34. (FIG. 22) The second front side matching layer 44 is preferably Parylene C sold by Specialty Coating Systems Inc. of Indianapolis, Ind., USA. This second front side matching layer 44 is preferably vapor deposited, as is well understood in the art, in a thickness of 15 μm and fixes and seals the acoustic stack 28. The flexible circuit 48 is attached to the acoustic stack 28. (FIG. 23)

The flexible circuit 48 previously attached to the piezoelectric ceramic/polymer composite array 34 is threaded down the catheter 22 and the acoustic stack 28 is positioned at the distal end 24 of the catheter 22 so that the guide-wire port 70 just extends beyond the distal end 24. (FIG. 24)

The traces 54 and ground electrode 56 of the flexible circuit 48 are soldered to the high-density interposer board for high-frequency applications 62 or board-to-board connector 66. (FIG. 25) Finally, the imaging system connection 30 is enclosed within the protective case 68. (FIG. 26)

The probe 10 as described herein is specifically designed to enable forward-looking IVUS images to be produced. The advantages of being able to see forward with the present probe 10, in one or more embodiments of the probe 10, when engaging in diagnostic and therapeutic activities, particularly with respect to such activities in connection with diagnosing or treating PAD, structural heart issues or coronary artery disease, are:

Electronic beam steering (no mechanical or moving parts);
No blind spot;
No electronic hardware components on or near the acoustic stack 28 or at or near the distal end 24 of the catheter 22;
Shorter solid length of the acoustic stack 28 (<5 mm vs 1 cm);
Distal end 24 of catheter 22 is less bulky and more flexible; and
Flexible circuit 48 eliminates the numerous cables inside of the catheter 22 to carry electrical signals; only one flexible circuit 48 (<50 um thick) that features all waveguides thus making the catheter 22 more flexible.

As described herein, the front side 36 of elements 20 is preferably flat. However, the front side 36 of elements 20 can be formed into a curved configuration so that the focus or field of view of the acoustic stack 28 can be manipulated to desired effect.

Further, although a flexible circuit 48 has been described as the preferred means to provide electrical signals to and receive electrical signals from the elements 20, individual conductors can also perform this function. For example, individual wires can run from the imaging system connection 30 to the individual elements 20 so that control signals from the IVUS control system 14 can be sent to respective elements 20 and electrical signals generated by respective elements 20 in response to receipt of reflected ultrasonic waves can be transmitted to the IVUS control system 14. In any event, a key feature of the present probe 10, in a preferred embodiment, is that this configuration and the configuration with the flexible circuit 48 provides that there be no electronics located at or near the distal end 24 of the catheter 22.

In use, the probe 10 must be inserted into a patient and moved to an area of interest in a surgical procedure. To do this, a patient is prepared by applying a local anesthetic to the skin of the area where the puncture will be made, typically the femoral artery in or near the groin or radial artery in the wrist. A puncture is then made in the skin with a needle to a desired artery. A guidewire is inserted into the arterial puncture and threaded through the patient's arteries to a desired location. A plastic sheath (with a stiffer plastic introducer inside it) is then threaded over the wire and pushed into the artery. The forward looking probe 10 is moved over the guidewire by threading the guidewire through the guidewire port 70. The probe 10 is advanced over the guidewire until the distal end 24 of the probe 10 is moved to the area of interest. Once the probe 10 is in an area of interest, it can be used to image the area in a direction forward to (distal) to the probe 10. The probe 10 may then be used to provide guidance and give feedback to help perform a number of procedures including angioplasty, PCI (percutaneous coronary intervention) angiography, balloon septostomy and angioplasty, electrophysiology studies, atherectomies, biopsies or ablation procedures.

In certain aspects of the disclosed invention, the imaging probe 10 itself may also serve as a delivery catheter for delivery of some type of a therapeutic device. Examples of such therapeutic devices include, but are not limited to, a stent, balloon, ablator or mechanical tools. Using the present probe 10 during a therapeutic procedure, the imaging probe 10 may be used both to identify a desired location and to deliver something (e.g., a stent or balloon) or position the probe 10 at the appropriate location to deliver therapy.

The present invention may also be used to produce data that can be deconstructed or analyzed to determine characteristics of the material (e.g., tissue) being imaged by the instant probe 10. For example, the data collected by the present probe 10 can be used to characterize tissue that produced the received reflected ultrasound signal. To do this, data must be collected at different "SEND" frequencies. As a result, the piezoelectric ceramic/polymer composite array 34 is operated at different frequencies. At each selected frequency, the piezoelectric ceramic/polymer composite array 34 emits an ultrasonic wave that is ultimately reflected and detected by the piezoelectric ceramic/polymer composite array 34. Differences in characteristics of the received signals at the different frequencies indicates characteristics of the tissue or material that produced the return echo signals.

For example, this tissue characterization process may include doing a spectral analysis on the received signal. This spectral analysis examines the energy of the received ultrasound signal at the various sent frequencies. Plaque deposits typically have different spectral signatures than other nearby tissue. So, these different spectral signatures are used to determine the tissue or material that produced the received signal. The signal processing may include, additionally or alternatively, statistical processing (e.g., averaging, filtering, FFT) of the received ultrasound signal in the time domain. Other signal processing techniques known in the art of tissue characterization may also be applied.

Further, the received ultrasonic data may be used to detect the velocity and direction of blood in front of the distal end 24 of the probe 10 by techniques well known in the art including, but not limited to, correlation-tracking the targets along the "forward looking" direction or by standard Doppler processing of a shift in frequency in the return ultrasonic echoes that correspond to target movement in directions parallel with the "forward looking" direction. The resulting calculated blood velocity may be displayed on the monitor 18 in connection with an IVUS image.

Although a probe 10 has been described herein as being used in arteries, the probe 10 may also be used in other vessels of all types that allow transmission of ultrasonic signals including without limitation, veins, gastrointestinal vessels and passages, urethra and ureters, ducts and cerebrospinal passages and canals.

Throughout this description, components have sometimes been described as occurring in pairs or singly or described in the plural or singular. Wherever occurrences of elements are described in the singular or plural, it is to be understood that unless stated otherwise, such elements may also be used in the opposite form as will be clear to those skilled in the art. In other words, if an element is described in the plural form, that element may also be used in the singular or vice versa unless specifically stated otherwise.

Although the present invention has been described with reference to preferred embodiments, workers skilled in the art will recognize that changes may be made in form and detail without departing from the spirit and scope of the invention.

As mentioned, the probe 10 of the present invention has been described in connection with certain embodiments, configurations and relative dimensions. However, the description above is not to be construed as being absolutely particular. It is to be understood that the description given herein has been given for the purpose of explaining and illustrating the probe 10 and is not intended to limit the scope of the invention. For example, the specific dimensions and configuration of the components of the probe 10 may be varied so long as the dimensions and configurations of the probe 10 provide the function of producing and receiving ultrasound signals for imaging and related purposes. Further, specific details of the acoustic stack 28 and its components, including the piezoelectric ceramic/polymer composite array 34, may be varied as will occur to those skilled in the art. Also, there are many materials and configurations that can be used in constructing the probe 10 that will be well understood by those skilled in the art including those being developed or that will be developed. In addition, it is clear than an almost infinite number of minor variations to the form and function of the disclosed probe 10 could be made and also still be within the scope of the invention. Consequently, it is not intended that the probe 10 be limited to the specific embodiments and variants of the invention disclosed. It is to be further understood that changes and modifications to the descriptions given herein will occur to those skilled in the art. Therefore, the scope of the invention should be limited only by the scope of the claims.

The invention claimed is:

1. A forward-looking imaging probe for creating ultrasound images distal to the imaging probe, the probe comprising:
   (a) a flexible elongate member having a distal end, a proximal end and a longitudinally extending axis;
   (b) an acoustic stack having a forward facing imaging surface, the forward facing imaging surface including a 1-dimensional piezoelectric array with a front side and a back side, the array made up of a plurality of elements, the acoustic stack located at the flexible elongate member distal end so that the forward facing imaging surface is perpendicular to the longitudinally extending axis, each respective element, in response to an electrical stimulus, transmitting ultrasonic waves in a direction normal to the forward facing imaging surface and distal to the flexible elongate member distal end, the respective elements receiving reflected ultrasonic waves and generating an electrical signal in response thereto; and
   (c) electrical conductors each attached to a respective element of the array and extending from the respective elements to the flexible elongate member proximal end,
   wherein the electrical conductors are part of a multi-layer flexible circuit having a distal end and a proximal end,
   wherein the multi-layer flexible circuit terminates at its distal end in projecting flaps that form a grounding clamp,
   wherein the distal end of the multi-layer flexible circuit is bonded to the back side of the array,
   wherein the projecting flaps that form the grounding clamp embrace the array and a first front side matching layer to hold these two components in place and electrically connect a front side of the first front side matching layer to the a ground electrode of the multi-layer flexible circuit,
   wherein the first front side matching layer is positioned across the front side of the array on the forward facing imaging surface, and
   wherein the front side of the first front side matching layer is a side of the first front side matching layer facing away from the array.

2. The device of claim 1 wherein the flexible elongate member is a catheter.

3. The device of claim 1 wherein the flexible elongate member is a guidewire.

4. The device of claim 1 wherein the array is made of a material chosen from the group consisting of lead magnesium niobate-lead titanate (PMN-PT), lead zirconate niobate-lead titanate (PZN-PT), lead zirconate titanate (PZT), lead indium niobate-lead magnesium niobate-lead titanate PIN-PMN-PT, manganese-doped PM N-PT (Mn:PMN) and manganese-doped PIN-PMN-PT.

5. The device of claim 1 wherein the array is operated at frequencies between 9 MHz to about 45 MHz.

6. The device of claim 1 wherein the array includes one selected from a group consisting of a 16-element array with 15 kerfs between the elements, a 32-element array with 31 kerfs between the elements, and a 64-element array with 63 kerfs between the elements.

7. The device of claim 6 wherein the width of each element is 19 µm.

8. The device of claim 6 wherein the width of the kerfs is 6 µm.

9. The device of claim 6 wherein the kerfs are polymer filled.

10. The device of claim 1 wherein the front side of the array is coated with a layer of metal so that one or more conductive matching layers can be bound to the front side and form a common ground.

11. The device of claim 1 wherein the array has a conductive first front side matching layer to provide efficient transmission of sound waves from the elements to the ambient environment.

12. The device of claim 11 wherein the first front side matching layer is a 2-3 µm silver epoxy applied to a thickness of about 25 µm thick.

13. The device of claim 12 wherein the first front side matching layer is chosen from the group consisting of epoxy, epoxy filled with one or more different fillers chosen from the group consisting of metal-impregnated graphite, glass ceramic, composite ceramic and metal chosen from the group consisting of copper, copper alloy, copper with graphite pattern embedded therein, magnesium, magnesium alloy, aluminum, aluminum alloy and gold.

14. The device of claim 11 wherein the array also includes a second front side matching layer that overlays and seals the first front side matching layer.

15. The device of claim 14 wherein the second front side matching layer is Parylene C.

16. The device of claim 14, wherein the second front side matching layer is a polymer material.

17. The device of claim 11, wherein the first front side matching layer is a conductive epoxy material and has a thickness equal to or less than one quarter of a resonant wavelength in the conductive epoxy material.

18. The device of claim 1 wherein the array includes a non-conductive backing layer that is located on the back side of the array to avoid reverberation or ringing of the array.

19. The device of claim 18 wherein the non-conductive backing layer is epoxy.

20. The device of claim 18, wherein the non-conductive backing layer is an epoxy material that enhances a round-trip attenuation of generated and returning signals, the epoxy material including at least one selected from a group consisting of a plasticizer and filling particles.

21. The device of claim 1 wherein the electrical conductors are part of a multi-layer flexible circuit having a distal end and a proximal end.

22. The device of claim 21 wherein the multi-layer flexible circuit terminates at its distal end in projecting flaps that form a grounding clamp.

23. The device of claim 22 wherein the distal end of the multi-layer flexible circuit is bonded to the back side of the array.

24. The device of claim 1 further comprising an imaging system connection located at the proximal end of the flexible elongate member, the imaging system connection providing an electrical connection to an imaging system.

25. The device of claim 1 further comprising a guide-wire port located at the distal end of the probe.

26. The device of claim 1, wherein the array includes a plurality of kerfs including a kerf between each element in the array, wherein a sum of a width of each element and a width of each kerf is equal to or less than half a resonant wavelength in an imaging medium.

27. A forward-looking imaging probe for creating ultrasound images distal to the imaging probe, the probe comprising:
 (a) a flexible elongate member having a distal end, a proximal end and a longitudinally extending axis;
 (b) an acoustic stack having a forward facing imaging surface, the forward facing imaging surface including a 1-dimensional piezoelectric array with a front side and a back side, the array made up of a plurality of elements, the acoustic stack located at the flexible elongate member distal end so that the forward facing imaging surface is perpendicular to the longitudinally extending axis, each respective element, in response to an electrical stimulus, transmitting ultrasonic waves in a direction normal to the forward facing imaging surface and distal to the flexible elongate member distal end, the respective elements receiving reflected ultrasonic waves and generating an electrical signal in response thereto;
 (c) electrical conductors each attached to a respective element of the array and extending from the respective elements to the flexible elongate member proximal end; and
 an imaging system connection located at the proximal end of the flexible elongate member, the imaging system connection providing an electrical connection to an imaging system,
 wherein the imaging system connection includes a high-density interposer board for high-frequency applications, a printed circuit board and a board-to-board connector electrically connected in serial.

28. A forward-looking imaging probe for creating ultrasound images distal to the imaging probe, the probe comprising:
 (a) a flexible elongate member having a distal end, a proximal end and a longitudinally extending axis;
 (b) an acoustic stack having a forward facing imaging surface, the forward facing imaging surface including a 1-dimensional piezoelectric array with a front side and a back side, the array made up of a plurality of elements, the acoustic stack located at the flexible elongate member distal end so that the forward facing imaging surface is perpendicular to the longitudinally extending axis, each respective element, in response to an electrical stimulus, transmitting ultrasonic waves in a direction normal to the forward facing imaging surface and distal to the flexible elongate member distal end, the respective elements receiving reflected ultrasonic waves and generating an electrical signal in response thereto;
 (c) electrical conductors each attached to a respective element of the array and extending from the respective elements to the flexible elongate member proximal end; and
 an imaging system connection located at the proximal end of the flexible elongate member, the imaging system connection providing an electrical connection to an imaging system,
 wherein the electrical conductors are part of a multi-layer flexible circuit having a distal end and a proximal end and the imaging system connection includes a board-to-board connector bonded directly to the flexible circuit at the proximal end of the flexible circuit.

* * * * *